United States Patent [19]

Pekkanen

[11] Patent Number: 4,476,114

[45] Date of Patent: Oct. 9, 1984

[54] IRON-SELENIUM PREPARATION

[75] Inventor: Timo J. Pekkanen, Vantaa, Finland

[73] Assignee: Orion-yhtymä Oy, Helsinki, Finland

[21] Appl. No.: 482,263

[22] Filed: Apr. 5, 1983

[30] Foreign Application Priority Data

Apr. 7, 1982 [FI] Finland .................................. 821233

[51] Int. Cl.³ ...................... A61K 33/04; A61K 31/70
[52] U.S. Cl. ..................................... 424/164; 424/180; 536/112; 536/113; 536/121
[58] Field of Search ................. 424/180, 164; 536/112, 536/113, 121

[56] References Cited

U.S. PATENT DOCUMENTS

| | | | |
|---|---|---|---|
| 2,820,740 | 1/1958 | London et al. | 424/180 |
| 3,022,221 | 2/1962 | Florano et al. | 424/180 |
| 3,076,798 | 2/1963 | Mueller et al. | 424/180 |

OTHER PUBLICATIONS

West et al., *Textbook of Biochemistry,* New York: Macmillan Company, 1966 pp. 1403–1404.
Dobbie et al., *Chemical Abstracts* vol. 79, 1973 p. 465, Abstract Number: 18830m.
Sugiura et al., *Chemical Abstracts* vol. 98, 1983 p. 172, Abstract Number: 1850n.

*Primary Examiner*—Johnnie R. Brown
*Assistant Examiner*—Elli Peselev
*Attorney, Agent, or Firm*—Burns, Doane, Swecker & Mathis

[57] ABSTRACT

A composition is provided for the treatment of deficiency state of iron and selenium in a mammal, which composition comprises a precipitate-free solution containing a deficiency-treating amount of an iron compound and a selenium compound, wherein the iron compound is ferric dextran, ferric polymaltose or the corresponding hydrolysates thereof, and the selenium compound is selenium dioxide or selenium selenite.

5 Claims, No Drawings

IRON-SELENIUM PREPARATION

This invention provides a new method for production of trace element solutions containing iron and selenium for treatment of animals and man.

Iron and selenium are essential elements, and their deficiency results in anaemia (iron deficiency) and impairment of ability to cope with different kinds of strain (selenium deficiency). Young, fast-growing animals such as cows, sheep and particularly pigs may suffer from iron and selenium deficiencies. A piglet receives only 1 mg iron daily from the milk of the sow, whereas the need is 7 ... 8 mg. In areas where the ground is especially poor in selenium, piglets do not receive enough selenium and are susceptible to various degenerative diseases.

In order to meet the iron and selenium requirements of a growing animal from birth onwards, piglets are today given iron and selenium, at the age of 1 ... 3 days, usually in the form of an intramuscular or subcutaneous injection. Iron is usually given as ferric dextran, corresponding to 100 ... 200 mg of iron. Selenium is administered as sodium selenite at a dosage of approx. 0.06 mg $Se^{+4}$/kg. Since the half-life of selenium in the organism is short and excess is not stored to any appreciable degree, a single selenium injection gives only a short-term protection.

Since a great number of piglets have to be injected with iron and selenium, a lot of work would be saved if the substances could be combined in a single injection solution. Lesions due to injections and the risk of infection would also be reduced by giving one injection instead of two.

Selenium and iron have not, so far, been combined in one solution because it is known that selenium forms insoluble compounds with iron. This is exploited in selenium analysis, for example. In fact public warnings have been given against introducing selenium salts or their solutions into the drinking water supply since selenium is precipitated in the presence of iron compounds.

It has now been found that when a soluble selenium compound is combined in an injection solution with a high molecular weight iron-polysaccharide complex, selenium does not, contrary to expectations, precipitate out.

It was also observed that injection of the new preparation into animals provides an additional source of selenium that can, surprisingly, be stored in the organism. The mechanism of storage is not clear, though the excess selenium is probably stored in the form of iron-selenium complexes.

In principle, any physiologically assimilable soluble selenium compound can be used in the new preparation. Sodium selenite and selenium dioxide are especially suitable.

The best iron-polysaccharide complexes are ferric dextran and ferric polymaltose.

The iron and selenium contents of the solution can be varied within a considerable range, according to whether the deficiency states are due primarily to lack of iron or to lack of selenium. The ratio of selenium to iron can be from $10^{-5}$ to $10^{-1}$ by weight, a ratio of $10^{-3}$ to $10^{-2}$ being especially suitable.

The solution is prepared simply by dissolving the selenium compound in an aqueous solution of iron polysaccharide (or corresponding hydrolysate) and adding water as necessary. Alternatively, the powdered substances can be mixed and water (or some other solvent) added later prior to use, or else a paste prepared. If desirable, other substances such as vitamin E can be added to the mixture.

The new type of preparation containing sodium selenite and ferric dextran was administered intramuscularly to three pigs, weight 15 ... 25 kg, suffering from selenium deficiency. Another three pigs suffering from selenium deficiency were given the same dose of sodium selenite. Serum selenium content and glutathione peroxidase enzyme activity were determined as a measure of the bioactivity of selenium in the organism. It was found that both the selenium content and glutathione peroxidase (gSH-Px) activity were significantly higher in the pigs given the preparation than in those given only selenium (Table 1). All the pigs were on the same diet throughout the test period.

TABLE 1

| No. | 0-sample gSH-Px IU/l | 0-sample Se ng/ml | at day 8 gSH-Px IU/l | at day 8 Se ng/ml | at day 15 gSH-Px IU/l | at day 15 Se ng/ml |
|---|---|---|---|---|---|---|
| 1 | 373 | 28 | 1065 | 53 | 632 | 40 |
| 2 | 298 | 19 | 796 | 47 | 437 | 32 |
| 3 | 325 | 23 | 926 | 47 | 484 | 34 |
| Mean | 332 | 23 | 926 | 49 | 518 | 35 |
| 4 | 374 | 20 | 1288 | 65 | 804 | 46 |
| 5 | 279 | 18 | 1365 | 63 | 752 | 49 |
| 6 | 429 | 26 | 1643 | 90 | 706 | 51 |
| Mean | 361 | 21 | 1432 | 73 | 754 | 49 |

Animals 1, 2 and 3 received 0.06 mg Se per kg body weight intramuscularly as sodium selenite.
Animals 4, 5 and 6 received 0.06 mg Se per kg body weight intramuscularly as sodium selenite combined with ferric dextran, 200 mg Fe per dose.

As shown in Table 1, the iron-selenium preparation provides a clearly observable increase in selenium bioactivity. After 8 days, the mean bioactivity in animals given selenium alone was 926 IU/l, whereas that in animals given the iron-selenium preparation was 1432 IU/l. After 15 days the corresponding figures were 518 IU/l and 754 IU/l. The serum selenium level also remained considerably elevated. The serum selenium level of animals given the preparation was unchanged after 15 days, whereas that of animals given selenium alone remained elevated for only 8 days.

Six newborn piglets weighing about 1 kg were given an intramuscular dose of 2 ml of the new iron-selenium preparation, each ml containing 100 mg $Fe^{+3}$ as ferric dextran and 0.15 mg $Se^{+4}$ as sodium selenite. It was found, contrary to expectations, that the serum levels of selenium and glutathione peroxidase were still high four weeks later (Table 2). This was in spite of the fact that the animals were fed on milk from a sow kept on a low-selenium diet during this period. Five similar piglets, given the same diet, formed the control group. The control animals were given 200 mg $Fe^{+3}$ ferric dextran intramuscularly at the same time as injection of the test group. Four weeks later, mean selenium levels of 55.4 ng/ml and a mean glutathione perioxidase activity of 710.8 IU/l were found in their serum. The differences between the mean values of the test group and the control group were statistically significant, the glutathione peroxidase difference at the 99% confidence interval and the Se difference at the 95% interval (Wilcoxson-Mann-Whitney rank sum test). Selenium and glutathione peroxidase activity levels in the sera of the piglets treated with the new preparation can still be considered sufficiently high four weeks after the treatment, whereas the corresponding values for the control animals indicate a deficiency state. It should be noted that the selenium dose of 0.3 mg/kg used in the trial is five times higher than the normal dose, and selenium is known to be rapidly eliminated from the organism.

TABLE 2

| No. | 0-values gSH-Px IU/l | 0-values Se ng/ml | +1 week gSH-Px IU/l | +1 week Se ng/ml | +2 weeks gSH-Px IU/l | +2 weeks Se ng/ml | +4 weeks gSH-Px IU/l | +4 weeks Se ng/ml |
|---|---|---|---|---|---|---|---|---|
| 7 | 467 | 53.6 | 520 | 68.9 | 648 | 70.2 | 1074 | 97.1 |
| 8 | n.d. | n.d. | 480 | 88.5 | 868 | 67.4 | 1010 | 69.5 |
| 9 | 402 | 76.4 | 601 | 105.2 | 953 | 86.3 | 1006 | 70.1 |
| 10 | 357 | 44.5 | 503 | 77.5 | 555 | 57.8 | 822 | 54.5 |
| 11 | n.d. | n.d. | 486 | 63.4 | 799 | 73.6 | 906 | 69.5 |
| 12 | 414 | 44.8 | 562 | 89.0 | 649 | 76.9 | 973 | 60.4 |
| Mean | 410 | 54.8 | 525.3 | 98.5 | 745.3 | 72.0 | 965.2 | 70.2 |

0.3 mg/Se/kg together with 200 mg $Fe^{+3}$
n.d. = not determined

In another study, two sows were kept on a low-selenium diet during the last four weeks of pregnancy and during lactation. The 25 piglets born alive were divided at the age of three days into two groups (12+13), both groups containing piglets from both sows. Blood samples were taken from all piglets for determination of selenium and glutathione peroxidase values and for blood cell counts. The test group (13 piglets) were given a subcutaneous injection of 200 mg (2 ml) $Fe^{+3}$ as ferric dextran, to which sodium selenite had been added to give a $Se^{+4}$ content of 0.15 mg/ml. The control group (12) received 200 mg $Fe^{+3}$ as ferric dextran without $Se^{+4}$. One piglet in the control group later died. After eight days, blood samples were taken from all piglets. Using an electronic counter it was found that the mean increase in the erythrocyte count in the test group was $1.76 \pm 0.44 + 10^{12}/l$ and in the control group $1.41 \pm 0.30 + 10^{12}/l$. The difference was statistically significant at the 95% confidence interval using the non-parametric Wilcoxson-Mann-Whitney rank sum test. Selenium has not previously been shown to increase erythrocyte synthesis. This is an important finding that will play a major role in both human and veterinary medicine. The use of selenium in combination with iron is likely to increase considerably. It has also been found that injection of iron plus selenium (200 mg $Fe^{+3}$ and 0.3 mg $Se^{+4}$ per animal) into piglets at the age of three days can, as was found earlier, keep serum selenium and glutathione peroxidase levels and growth normal for at least for 3 weeks, whereas the control animals (200 mg $Fe^{+3}$ per animal) were by this time suffering from severe selenium deficiency, as shown by a retardation in weight increase. Selenium is probably stored as an iron-selenium complex, which explains the unexpected sufficiency of a single dose given at an early stage up to a weight of about 8 ... 10 kg.

The results show that the new iron-selenium preparation has quite surprising depot and long-term effects on the organism, as well as possessing surprisingly high bioactivity.

The following examples refer to the new type of preparation.

EXAMPLE 1

Composition

Sodium selenite corresponding $Se^{4+}$: 0.150 mg
Ferric dextran hydrolysate corresponding $Fe^{3+}$: 100.0 mg
Sterile water: up to 1.0 ml Sodium selenite corresponding 150 mg selenium was dissolved in 5 ml sterile water and the solution was added to the solution of ferric dextran hydrolysate. The solution was diluted with sterile water to 1 liter and passed through a filtermembrane or glasclinker for removing the particles. The filtrate was filled in glass-ampoule or injection-bottles sterilized with hot-air. The ready-packed injection solutions were sterilized by autoclaving.

EXAMPLE 2

Composition

Sodium selenite corresponding $Se^{4+}$: 0.150 mg
Ferric polymaltose corresponding $Fe^{3+}$: 100.0 mg
Sterile water: up to 1.0 ml Ferric hydroxydipolymaltose complex corresponding 100 mg of ferric was dissolved in 500 ml sterile water and sodium selenite was added. The solution was diluted with sterile water to 1 liter, it was filtered and filled to its receptacles and sterilized.

EXAMPLE 3

Composition

Selene dioxide corresponding $Se^{4+}$: 0.1 mg
Ferric dextran hydrolysate corresponding $Fe^{3+}$: 100.0 mg
Sterile water: up to 10.0 ml The injection solution was prepared as in example 1.

EXAMPLE 4

Composition

Sodium selenite corresponding $Se^{4+}$: 0.2 mg
Ferric polymaltose corresponding $Fe^{3+}$: 100.0 mg A homogeneous powder-mixture was prepared by known means. The powder-mixture can be granulated with solvents.

EXAMPLE 5

Sodium selenite corresponding $Se^{4+}$: 0.06 mg
Ferric dextran hydrolysate corresponding $Fe^{3+}$: 100.0 mg
Sterile water according to need
Polyethyleneglycols Selenium and ferric compounds were dissolved in a small amount of water. Polyethyleneglycol was added in the water solution with effective mixing until the paste was formed.

I claim:

1. An injectable trace element solution comprising a precipitate-free aqueous solution containing a deficiency-treating amount of an iron compound and a selenium compound, wherein the iron compound is ferric dextran, ferric polymaltose or the corresponding hydrolysates thereof, and the selenium compound is selenium dioxide or sodium selenite, the ratio of selenium to iron being from $10^{-5}$ to $10^{-1}$ by weight.

2. The solution of claim 1 wherein the selenium compound is sodium selenite.

3. The solution of claim 1 wherein the iron compound is ferric dextran or the corresponding hydrolysate.

4. The solution of claim 1 wherein the ratio of selenium to iron is from $10^{-3}$ to $10^{-2}$ by weight.

5. A method of treating a deficiency state of iron and selenium in a mammal comprising administering to the mammal a deficiency-treating amount of the solution of claim 1.

* * * * *